(12) United States Patent
Jetti et al.

(10) Patent No.: US 10,738,071 B2
(45) Date of Patent: Aug. 11, 2020

(54) POLYMORPHIC FORMS OF SOFOSBUVIR

(71) Applicant: Mylan Laboratories Limited, Hyderabad (IN)

(72) Inventors: Ramakoteswara Rao Jetti, Hyderabad (IN); Hemant Malhari Mande, Hyderabad (IN); Anjaneyaraju Indukuri, Hyderabad (IN); Narasimha Murty Pilli, Hyderabad (IN); Ravi Venkata Naga Vikas Chandra Dev, Hyderabad (IN); Vijaya Krishna Ravi, Hyderabad (IN)

(73) Assignee: Mylan Laboratories Limited (IN)

( * ) Notice: Subject to any disclaimer, the term of this patent is extended or adjusted under 35 U.S.C. 154(b) by 0 days.

(21) Appl. No.: 16/085,796

(22) PCT Filed: Mar. 17, 2017

(86) PCT No.: PCT/IN2017/050096
§ 371 (c)(1),
(2) Date: Sep. 17, 2018

(87) PCT Pub. No.: WO2017/158624
PCT Pub. Date: Sep. 21, 2017

(65) Prior Publication Data
US 2019/0100550 A1    Apr. 4, 2019

(30) Foreign Application Priority Data
Mar. 17, 2016  (IN) .............. 201641009411

(51) Int. Cl.
*C07H 19/10* (2006.01)
*A61K 31/7072* (2006.01)
*C07H 1/00* (2006.01)
*A61P 31/14* (2006.01)

(52) U.S. Cl.
CPC ......... *C07H 19/10* (2013.01); *A61K 31/7072* (2013.01); *C07H 1/00* (2013.01); *A61P 31/14* (2018.01); *C07B 2200/13* (2013.01)

(58) Field of Classification Search
None
See application file for complete search history.

(56) References Cited

U.S. PATENT DOCUMENTS

| | | | |
|---|---|---|---|
| 9,340,568 B2 | 5/2016 | Casteel et al. | |
| 9,845,335 B2 * | 12/2017 | Gaboardi | ............... G01L 15/00 |
| 2017/0015696 A1 | 1/2017 | Palacios et al. | |
| 2017/0137453 A1 | 5/2017 | Albrecht et al. | |
| 2017/0296570 A1 | 10/2017 | Martin et al. | |

FOREIGN PATENT DOCUMENTS

| | | | |
|---|---|---|---|
| CA | 2968137 A1 | 7/2016 | |
| CN | 104447924 A | 3/2015 | |
| CN | 105732751 A | 7/2016 | |
| WO | 2010135569 A1 | 11/2010 | |
| WO | WO2011/123645 | * 10/2011 | ............ C07H 19/06 |
| WO | 2016008461 | 1/2016 | |
| WO | 2016023906 | 2/2016 | |
| WO | 2016035006 | 3/2016 | |
| WO | 2016038542 | 3/2016 | |
| WO | 2016097173 | 6/2016 | |
| WO | 2016156512 | 10/2016 | |
| WO | 2016189443 | 12/2016 | |
| WO | 2017158624 | 9/2017 | |
| WO | 2017190715 | 11/2017 | |
| WO | 2018025195 | 2/2018 | |

OTHER PUBLICATIONS

International Search Report, PCT/IN2017/050096.
Caira M R, Crystalline Polymorphism of Organic Compounds, Topics in Current Chemistry, Jan. 1, 1998, p. 163-208.

* cited by examiner

*Primary Examiner* — Eric Olson

(57) ABSTRACT

The present disclosure provides novel crystalline sofosbuvir form-M3 and a process for the preparation of sofosbuvir form-M3. The crystalline sofosbuvir form-M3 disclosed herein may be useful in the formulation of pharmaceutical dosage forms.

20 Claims, 3 Drawing Sheets

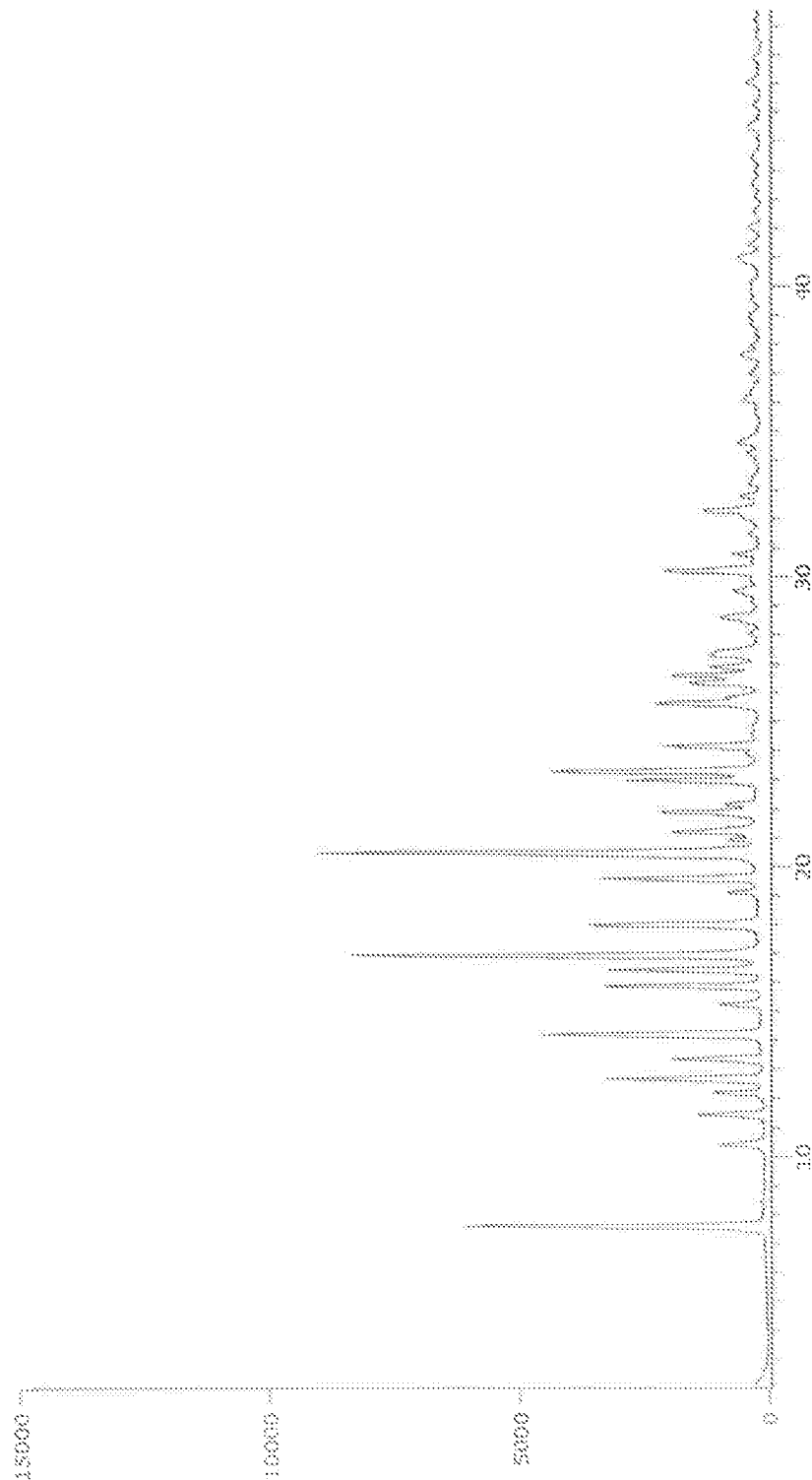
Figure 1-Powder X-ray diffraction pattern of crystalline sofosbuvir Form-M3

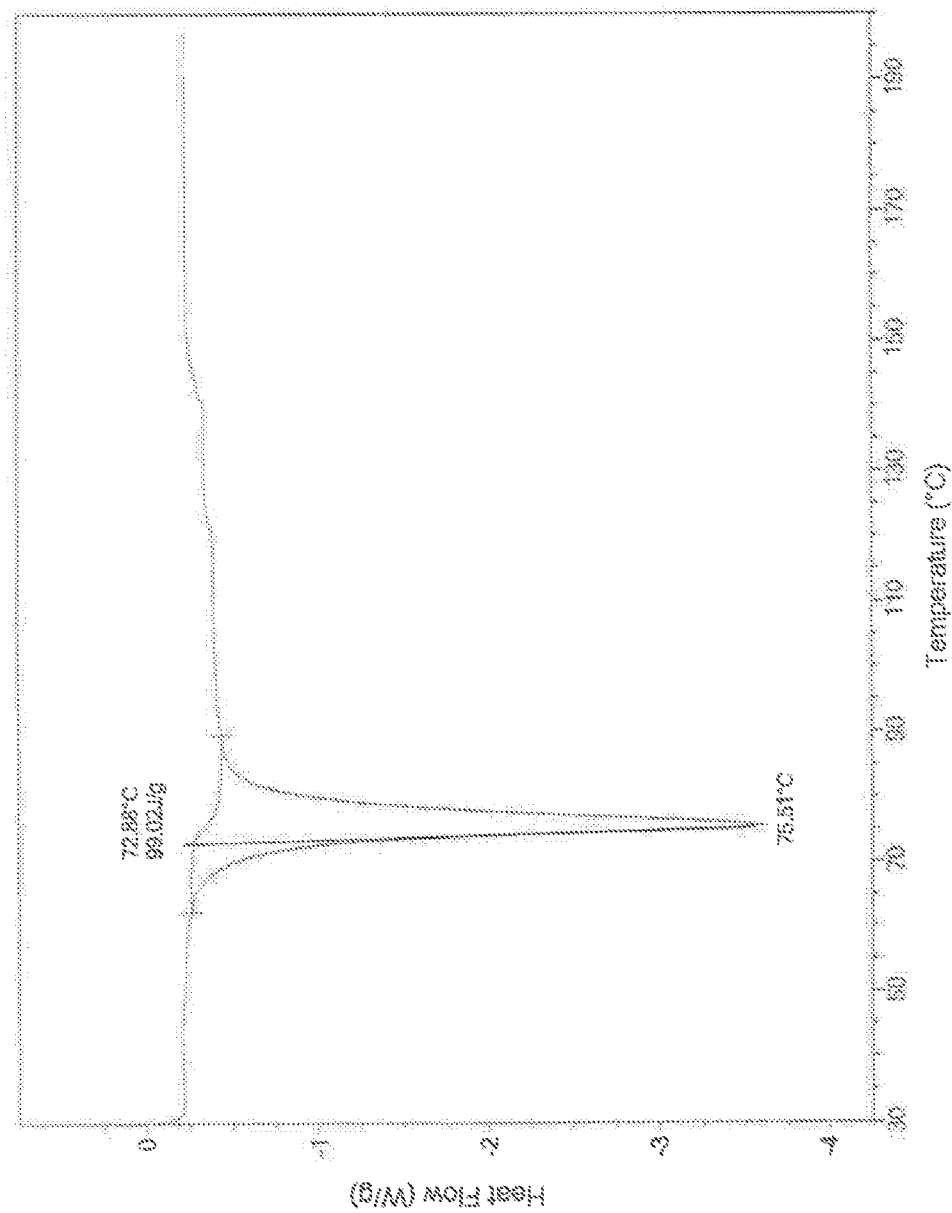
Figure 2- illustration of differential scanning calorimetry ("DSC") curve of crystalline sofosbuvir Form-M3

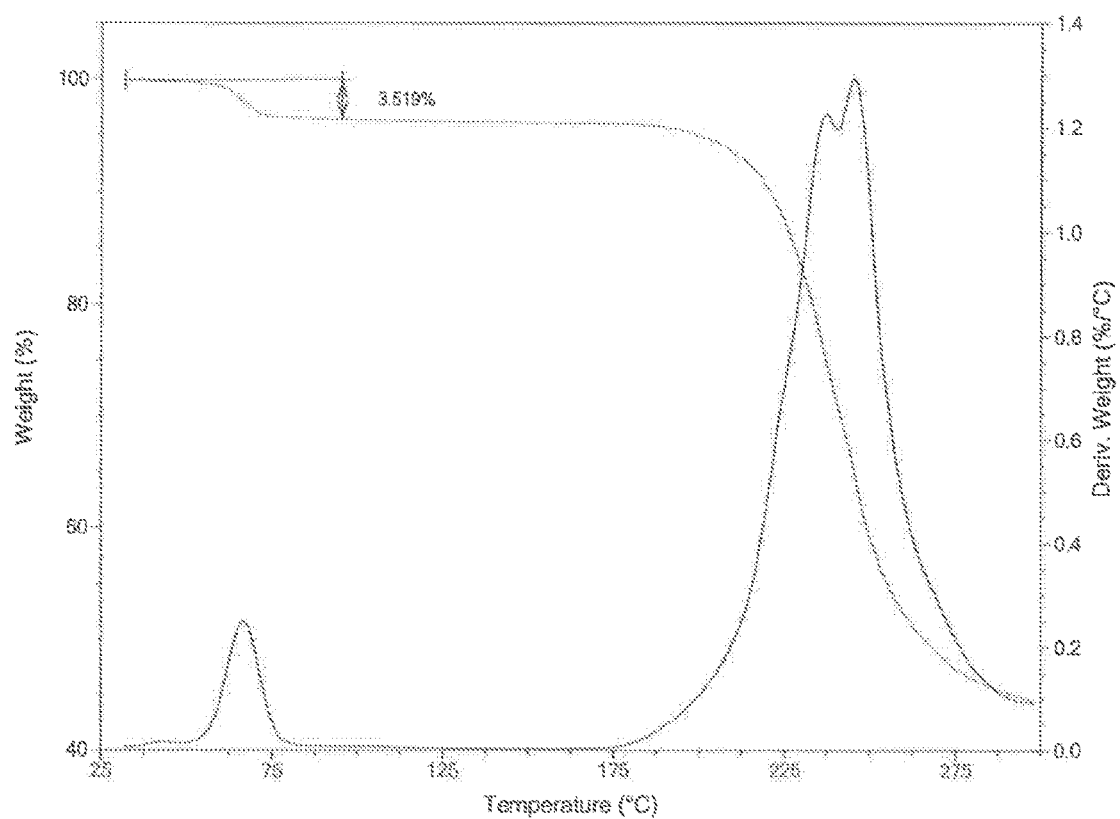
Figure 3- illustration of thermo gravimetric analysis ("TGA") curve of crystalline sofosbuvir Form-M3

POLYMORPHIC FORMS OF SOFOSBUVIR

CROSS-REFERENCE TO RELATED APPLICATIONS

This application is a U.S. National Stage application under 35 U.S.C. §371 of International Patent Application No. PCT/IN2017/050096, Mar. 17, 2017, which claims the benefit of Indian provisional patent application No. 201641009411 filed on Mar. 17, 2016, of which is hereby incorporated by reference in its entirety.

BACKGROUND OF THE INVENTION

Field of the Invention

The present disclosure relates to novel crystalline forms of sofosbuvir and a process for the preparation thereof.

Background of the Invention

Some nucleoside phosphoramidates inhibit RNA-dependent RNA viral replication and, in some instances, are particularly useful as inhibitors of hepatitis C virus (HCV) NS5B polymerase. The reduction in NS5B polymerase activity suppresses HCV replication. Due to this inhibitory activity, nucleoside phosphoramidates are often used for the treatment of hepatitis C infection. Sofosbuvir is one such nucleoside phosphoramidate which is commonly prescribed to treat HCV.

Chemically, sofosbuvir is known as (S)-isopropyl 2-((S)-(((2R,3R,4R,5R)-5-(2,4-dioxo3,4-dihydropyrimidin-1(2H)-yl)-4-fluoro-3-hydroxy-4-methyltetrahydrofuran-2yl)methoxy)-(phenoxy)phosphorylamino)propanoate and has the following chemical structure (Formula 1):

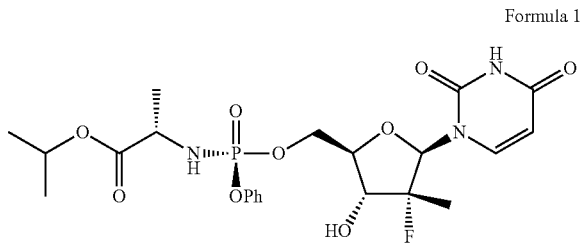 [SMILES: CC(C)OC(=O)[C@H](C)N[P@](=O)(OC[C@H]1O[C@@H](n2ccc(=O)[nH]c2=O)[C@](C)(F)[C@@H]1O)Oc1ccccc1]

Formula 1

Sofosbuvir is marketed in the United States by Gilead Sciences under the brand name SOVALDI™. It is also marketed as a combination product with ledipasvir as HARVONI® and in combination with velpatasvir as EPCLUSA® by the same company.

U.S. Pat. No. 7,964,580, which is hereby incorporated by reference for the preparation of sofosbuvir, discloses sofosbuvir and a process for the preparation thereof. PCT Publication No. WO2010135569A1, which is hereby incorporated by reference for the disclosure of sofosbuvir physical forms, discloses amorphous and crystalline forms of sofosbuvir.

The inventors of the present disclosure have developed a novel crystalline form of sofosbuvir and a process for the preparation thereof.

SUMMARY OF THE INVENTION

In one aspect, the present invention provides crystalline sofosbuvir form-M3.

In one embodiment, the crystalline sofosbuvir form-M3 disclosed herein may be characterized by a PXRD pattern having peaks at 2θ angle positions of 7.61, 16.92, and 20.47±0.2°.

The crystalline sofosbuvir form-M3 may be further characterized by a PXRD pattern having peaks at 2θ angle positions of 7.61, 14.19, 16.92, 17.98, 19.58, 20.47, and 23.27±0.2°.

The crystalline sofosbuvir form-M3 may be yet further characterized by a PXRD pattern as shown in FIG. 1.

In another aspect, the present invention provides a process for preparing crystalline sofosbuvir form-M3.

In one embodiment, crystalline sofosbuvir form-M3 may be prepared by a process that includes the steps of:
1. dissolving sofosbuvir in a solvent to form a solution;
2. adding an anti-solvent to the solution; and
3. isolating crystalline sofosbuvir form-M3.

Within the context of this embodiment, the solvent is a water-miscible solvent, which may be, for example, methanol, ethanol, isopropanol, 1-butanol, isobutanol, 1-pentanol, acetone, acetonitrile, N,N-dimethylformamide, dimethylsulfoxide, 1,2-dimethoxyethane, or mixtures thereof.

In some embodiments, the solvent may be a mixture of a water-miscible solvent and water.

Within the context of this embodiment, the anti-solvent is water.

In some particularly useful embodiments, the solution is stirred after adding the anti-solvent and before the isolating crystalline sofosbuvir form-M3.

In some particularly useful embodiments, the solution is seeded with crystalline sofosbuvir form-M3 after adding an anti-solvent and before isolating crystalline sofosbuvir form-M3.

In another embodiment, crystalline sofosbuvir form-M3 may be prepared by a process that includes the steps of:
1. dissolving sofosbuvir in a solvent to form a solution;
2. adding an anti-solvent to the solution;
3. seeding with crystalline sofosbuvir form-M3;
4. adding additional anti-solvent to the solution; and
5. isolating crystalline sofosbuvir form-M3.

Within the context of this embodiment, the solvent may be, for example, methanol, ethanol, isopropanol, 1-butanol, isobutanol, 1-pentanol, N,N-dimethylformamide, dimethyl sulfoxide, 1,2-dimethoxyethane, acetone, or mixtures thereof.

In some particularly useful embodiments, the dissolving step is carried out at ambient temperatures, for example, from about 25° C. to about 35° C., or at an elevated temperatures, for example, from about 50° C. to about 70° C. In other embodiments, the solution is heated after the dissolving step, for example, from about 50° C. to about 70° C. In such embodiments where the solution of sofosbuvir is heated, it may be useful to cool the solution before crystalline sofosbuvir form-M3 is isolated. This cooling step may occur at any time. In particularly useful embodiments, the solution is cooled before an anti-solvent is added.

Within the context of this embodiment, the anti-solvent is water.

In another embodiment, crystalline sofosbuvir form-M3 may be prepared by a process that includes the steps of:
1. dissolving sofosbuvir in a solvent to get a first solution;
2. suspending seeds of sofosbuvir form-M3 in an anti-solvent to get a seeded anti-solvent solution;
3. combining the first solution and the seeded anti-solvent solution to form a second solution; and
4. isolating sofosbuvir form-M3.

Within the context of this embodiment, the solvent may be, for example, methanol, ethanol, isopropanol, 1-butanol, isobutanol, 1-pentanol, N,N-dimethylformamide, dimethyl sulfoxide, 1,2-dimethoxyethane, acetone, or mixtures thereof.

In some particularly useful embodiments, the dissolving step is carried out at ambient temperatures, for example, from about 25° C. to about 35° C., or at an elevated temperatures, for example, from about 50° C. to about 70° C. In other embodiments, the solution is heated after the dissolving step, for example, from about 50° C. to about 70° C. In such embodiments where the solution of sofosbuvir is heated, it may be useful to cool the solution before crystalline sofosbuvir form-M3 is isolated. This cooling step may occur at any time. In particularly useful embodiments, the solution is cooled before combining the first solution and the seeded anti-solvent solution.

Within the context of this embodiment, the anti-solvent is water.

Within the context of the present invention, the crystalline sofosbuvir form-M3 may be incorporated into a pharmaceutical dosage form, for example, a tablet or a capsule. The pharmaceutical dosage form may further contain pharmaceutically acceptable excipients.

BRIEF DESCRIPTION OF THE FIGURES

Further aspects of the present disclosure together with additional features contributing thereto and advantages accruing there from will be apparent from the following description of embodiments of the disclosure which are shown in the accompanying drawing figures wherein:

FIG. 1 is an X-ray powder diffractogram of crystalline sofosbuvir form-M3;

FIG. 2 is a differential scanning calorimetry ("DSC") thermogram of crystalline sofosbuvir form-M3; and FIG. 3 is a thermogravimetric analysis ("TGA") thermogram of crystalline sofosbuvir form-M3.

DETAILED DESCRIPTION OF THE INVENTION

The present disclosure provides crystalline sofosbuvir form-M3 and a process for the preparation thereof.

In one aspect, the present invention provides crystalline sofosbuvir form-M3.

The crystalline sofosbuvir form-M3 disclosed herein may be characterized by X-ray powder diffraction. Therefore, samples of crystalline sofosbuvir form-M3 were analyzed on a PANalytical, X'pert PRO powder diffractometer equipped with goniometer of θ/θ configuration and X'Celerator detector. The Cu-anode X-ray tube was operated at 40 kV and 30 mA. The experiments were conducted over the 2θ range of 2.0°-50.0°, 0.030° step size and 50 seconds step time.

As disclosed herein, crystalline sofosbuvir form-M3 may be characterized by a powder X-ray diffraction pattern having peaks at 7.61, 16.92, and 20.47±0.2 °2θ.

Crystalline sofosbuvir form-M3 may be further characterized by a powder X-ray diffraction pattern having peaks at 7.61, 14.19, 16.92, 17.98, 19.58, 20.47, and 23.27±0.2 °2θ.

Crystalline sofosbuvir form-M3 may be further characterized by a powder X-ray diffraction pattern having peaks at 7.61, 8.45, 10.41, 11.44, 12.20, 12.66, 13.35, 14.19, 15.23, 15.87, 16.42, 16.92, 17.98, 19.10, 19.58, 20.47, 20.91, 21.19, 21.88, 22.15, 22.96, 23.27, 23.86, 24.15, 24.54, 25.62, 26.31, 26.59, 26.89, 27.26, 27.44, 28.03, 28.59, 29.13, 29.53, 30.19, 30.78, 31.45, 32.28, 32.76, 33.18, 34.22, 34.59, 36.04, 36.96, 37.65, 37.93, 38.99, 39.44, 40.14, 40.79, 41.00, 41.42, 41.99, 42.56, 43.08, 43.60, 44.42, 45.43, 46.26, 47.03, 47.86, 48.65, and 49.18±0.2 °2θ.

Crystalline sofosbuvir form-M3 may be further characterized by the powder X-ray diffraction pattern shown in FIG. 1.

The crystalline sofosbuvir form-M3 disclosed herein may also be characterized by differential scanning calorimetry (DSC). Therefore, samples of crystalline sofosbuvir form-M3 were analyzed on a TA Q1000 (TA instruments). The experiments were performed at a heating rate of 10° C./min over a temperature range of 30° C.-250° C., purging with nitrogen at a flow rate of 50 mL/min. Standard aluminum pans covered by lids with three pinholes were used.

Crystalline sofosbuvir form-M3 may be characterized by a DSC thermogram having a peak at about 72.88° C.-75.51° C. It is believed that the peak at 72.88° C.-75.51° C. is due to melting.

The crystalline sofosbuvir form-M3 may be further characterized by the DSC thermogram shown in FIG. 2.

Within the context of the invention, the term "about" when modifying an absolute measurement, such as time, mass, or volume, is meant to mean the recited value plus or minus 10% of that value. Within the context of the invention, the term "about" when modifying a temperature measurement is meant to mean the recited temperature plus or minus five degrees.

The crystalline sofosbuvir form-M3 disclosed herein may also be characterized by thermogravimetric analysis (TGA). Therefore, samples of crystalline sofosbuvir form-M3 were analyzed on a TA Q5000 IR (TA instruments). The experiments were performed at a heating rate of 10.0° C./min over a temperature range of ambient—300° C., purging with nitrogen at a flow rate of 25 mL/min.

Within the context of this invention, the crystalline sofosbuvir form-M3 disclosed herein may be characterized by the TGA thermogram shown in FIG. 3. It is believed that the measured decrease of 3.519% shown in FIG. 3 is due to loss of water.

Crystalline sofosbuvir form-M3 disclosed herein may also be analyzed for water content.

Water content was determined on an 841 Titrando Karl-Fischer titrator (Metrohm) by placing 40 mL dehydrated methanol in the titration vessel and titrating with a standardized reagent to reach the electrometric endpoint. A sample (e.g., 0.20 g sofosbuvir form-M3) was added, the mixture was stirred for 1 minute, then titrated to the endpoint with a Karl-Fischer reagent. For each determination, fresh methanol was used. The following calculations may be used to determine water content of each sample:

$$\text{Water content (\% w/w)} = \frac{V \times F \times 100}{W \times 1000}$$

For the above calculation, V is the volume of Karl-Fischer reagent consumed (measured in milliliters (mL)), F is the water equivalence factor (in milligrams per milliliter (mg/mL)), and W is the weight of sample (measured in grams (g)).

In another aspect, the present invention provides a method for the preparation of crystalline sofosbuvir form-M3.

In one embodiment, crystalline sofosbuvir form-M3 may be prepared by a process that includes the steps of:

a) dissolving sofosbuvir in a solvent to form a solution;

b) adding an anti-solvent; and
c) isolating crystalline sofosbuvir form-M3.

According to this embodiment, sofosbuvir is dissolved in a solvent. This step may be performed at ambient temperatures, for example, from about 25° C. to about 35° C., or at an elevated temperatures, for example, from about 50° C. to about 70° C.

The starting sofosbuvir material may be any polymorphic form (e.g., crystalline, amorphous) and be prepared by any prior-art process. For example, it may be prepare by processes disclosed in U.S. Pat. No. 8,618,076 or PCT Publication No. WO2015097605.

Within the context of this embodiment, the solvent is a water-miscible solvent. Examples of suitable water-miscible solvents include, but are not limited to, methanol, ethanol, isopropanol, 1-butanol, isobutanol, 1-pentanol, acetone, acetonitrile, N,N-dimethylformamide, dimethylsulfoxide, 1,2-dimethoxyethane, and mixtures thereof. One of skill in the art will recognize numerous water-miscible solvents that may be useful within the context of this embodiment.

Optionally, a small amount of water may be added to the solvent to facilitate dissolution of sofosbuvir. For example, in some embodiments a mixture of water and 1,2-dimethoxyethane is used to dissolve sofosbuvir. Within the context of this embodiment, using a solvent to water ratio of about 1:2 to 3:1 may be useful. In particularly useful embodiments, a 1.5:1 mixture of 1,2-dimethoxyethane to water is used to dissolve sofosbuvir.

Next, an anti-solvent is added to the solution. In particularly useful embodiments, water is used as the anti-solvent.

In some embodiments, it is found that adding the anti-solvent slowly and then stirring the solution for an extended period of time is particularly useful. For example, in some embodiments, the solution is stirred for about 10 hours to about 20 hours.

Next, crystalline sofosbuvir form-M3 is isolated as a solid. This may be carried out according to methods well known in the art such as, for example, decantation, filtration (e.g., by gravity or suction), centrifugation, slow evaporation, or any combination thereof. The obtained solid may be further treated to obtain crystalline sofosbuvir form-M3 with desired pharmaceutical characteristics. For example, the solid may be washed and dried under vacuum. In particularly useful embodiments, the solid is isolated by filtration followed by washing with water and drying. In some particularly useful embodiments, it is found that drying at 60° C.-70° C. for about 3 hours results in stable crystalline sofosbuvir form-M3.

At any point after dissolving sofosbuvir and isolating the final crystalline product, the solution may be optionally seeded with crystalline sofosbuvir form-M3. In such embodiments, stirring the reaction mass at temperature of about 20° C. to about 30° C. for an additional 12 hours to about 17 hours after seeding but before isolating the final product, in some embodiments, is found to be particularly useful.

In another embodiment, crystalline sofosbuvir form-M3 may be prepared by a process that includes the steps of:
a) dissolving sofosbuvir in a solvent to form a solution;
b) adding an anti-solvent to the solution;
c) seeding with crystalline sofosbuvir form-M3;
d) adding additional anti-solvent to the solution; and
e) isolating crystalline sofosbuvir form-M3.

According to this embodiment, sofosbuvir is dissolved in a solvent to form a solution.

The starting sofosbuvir material may be any polymorphic form (e.g., crystalline, amorphous) and be prepared by any prior-art process. For example, it may be prepare by processes disclosed in U.S. Pat. No. 8,618,076 or PCT Publication No. WO2015097605.

Within the context of this embodiment, the solvent is a water-miscible solvent. Examples of suitable water-miscible solvents include, but are not limited to, methanol, ethanol, isopropanol, 1-butanol, isobutanol, 1-pentanol, acetone, acetonitrile, N,N-dimethylformamide, dimethyl sulfoxide, 1,2-dimethoxyethane, and mixtures thereof. In particularly useful embodiments, N,N-dimethylformamide, methanol, ethanol, isopropanol, acetone, dimethylsulfoxide, or mixtures thereof are used as solvent. One of skill in the art will recognize numerous water-miscible solvents that may be useful within the context of this embodiment.

Anti-solvent may then be added to the solution. Within the context of this embodiment, one example of a useful anti-solvent is water.

Next, the solution may be seeded with crystalline sofosbuvir form-M3.

Additional anti-solvent, e.g., water, may then be added to the solution.

Next, crystalline sofosbuvir form-M3 is isolated. This may be carried out according to methods well known in the art, for example, by decantation, filtration (e.g., by gravity or suction), centrifugation, or any combination thereof. Optionally, the solid may be washed and dried under vacuum. In particular useful embodiments of the present invention, the solid is isolated by filtration followed by washing with water and is subsequently dried.

Optionally, the solution of sofosbuvir may be heated to an elevated temperature. This may be carried out by carrying out dissolving step at an elevated temperature or heating the solution after the solution of sofosbuvir is formed. In particularly useful embodiments, the solution of sofosbuvir is warmed to a temperature of about 50° C. to about 70° C., which may include temperatures of 50° C.-70° C., 50° C.-65° C., 50° C.-60° C., 50° C.-55° C., 55° C.-70° C., 55° C.-65° C., 55° C.-60° C., 60° C.-70° C., 60° C.-65° C., or 65° C.-70° C.

In embodiments, where the solution of sofosbuvir is heated to an elevated temperature, the solution may be cooled before isolating the crystalline sofosbuvir form-M3. For example, in some embodiments, the solution is cooled to a temperature of about 20° C. to about 35° C. This may be carried out at any step. In particularly useful embodiments, the solution is cooled before adding the anti-solvent.

In some embodiments, it is found that stirring the second solution at a temperature of about 20° C. to about 35° C. for about 10 hours to about 15 hours before isolating crystalline sofosbuvir form-M3 is particularly useful.

In another embodiment, crystalline sofosbuvir form-M3 may be prepared by a process that includes the steps of:
a) dissolving sofosbuvir in a solvent to get a first solution;
b) suspending seeds of sofosbuvir form-M3 in an anti-solvent to get a seeded anti-solvent solution;
c) combining the first solution and the seeded anti-solvent solution to get a second solution; and
d) isolating sofosbuvir form-M3.

According to this embodiment, sofosbuvir is dissolved in a solvent to get a first solution. This step may be performed at ambient temperatures, for example, from about 25° C. to about 35° C., or at an elevated temperature, for example, from about 50° C. to about 70° C.

The starting sofosbuvir material may be any polymorphic form (e.g., crystalline, amorphous) and be prepared by any prior-art process. For example, it may be prepare by processes disclosed in U.S. Pat. No. 8,618,076 or PCT Publication No. WO2015097605.

Within the context of this embodiment, the solvent is a water-miscible solvent. Examples of suitable water-miscible solvents include, but are not limited to, methanol, ethanol, isopropanol, 1-butanol, isobutanol, 1-pentanol, acetone, acetonitrile, N,N-dimethylformamide, dimethyl sulfoxide, 1,2-dimethoxyethane, and mixtures thereof. In particularly useful embodiments, N,N-dimethylformamide, methanol, ethanol, isopropanol, acetone, dimethylsulfoxide, or mixtures thereof are used as solvent. One of skill in the art will recognize numerous water-miscible solvents that may be useful within the context of this embodiment.

Next, seeds of crystalline sofosbuvir form-M3 are suspended in an anti-solvent to form a seeded anti-solvent solution.

The first solution and the seeded anti-solvent solution may then be combined to form a second solution.

Next, crystalline sofosbuvir form-M3 is isolated. This may be carried out according to methods well known in the art, for example, decantation, filtration (e.g., by gravity or suction), centrifugation, or any combination thereof. Optionally, the solid may be washed and dried under vacuum. In particular useful embodiments of the present invention, the solid is isolated by filtration followed by washing with water and is subsequently dried.

In some embodiments, it is found that stirring the second solution at a temperature of about 20° C. to about 35° C. for about 10 hours to about 15 hours before isolating crystalline sofosbuvir form-M3 is particularly useful.

Optionally, the solution of sofosbuvir may be heated to an elevated temperature. This may be carried out by carrying out dissolving step at an elevated temperature or heating the solution after the solution of sofosbuvir is formed. In particularly useful embodiments, the solution of sofosbuvir is warmed to a temperature of about 50° C. to about 70° C., which may include temperatures of 50° C.-70° C., 50° C.-65° C., 50° C.-60° C., 50° C.-55° C., 55° C.-70° C., 55° C.-65° C., 55° C.-60° C., 60° C.-70° C., 60° C.-65° C., or 65° C.-70° C.

In embodiments, where the solution of sofosbuvir is heated to an elevated temperature, the solution may be cooled before isolating the crystalline sofosbuvir form-M3. For example, in some embodiments, the solution is cooled to a temperature of about 20° C. to about 35° C. This may be carried out at any step. In particularly useful embodiments, the solution is cooled before adding the anti-solvent.

Crystalline sofosbuvir form-M3 disclosed herein may, in some embodiments, exhibit long-term physical and chemical stability. The physical and chemical stability of sofosbuvir form-M3 was determined by storing the samples at 25±2° C./60±5% relative humidity (RH) and at 40±2° C./75±5% RH for 6 months. The samples were tested to determine water content, detect degradation crystalline form by PXRD analysis, and measure purity by HPLC analysis. HPLC analysis was performed by the parameters listed below:

Chromatographic Conditions:
Column: Symmetry C18, 150×4.6 mm, 3.5 μm
Detector: UV at 260 nm
Flow rate: 1.0 mL/minute
Injection volume: 20.0 μL
Column oven temperature: 45° C.
Sample temperature: 10° C.
Run time: 30 minutes
Acquisition time: 25 minutes Diluent:
Water: Acetonitrile (80:20) % v/v As an example, Table 1 below discloses data collected on sofosbuvir form-M3 under various storage conditions. The PXRD data show that crystalline sofosbuvir form-M3 has no significant change in PXRD pattern, no significant change in purity, and no significant change in moisture content for up to six months when stored at 25±2° C./60±5% relative humidity (RH) and at 40±2° C./75±5% relative humidity (RH).

TABLE 1

| Storage Condition | Water content (%) | HPLC Purity (%) | PXRD |
|---|---|---|---|
| at 25 ± 2° C./60 ± 5% RH | | | |
| Initial | 3.59 | 99.92 | form-M3 |
| 1 months | 3.39 | 99.90 | form-M3 |
| 2 months | 3.45 | 99.90 | form-M3 |
| 3 months | 3.35 | 99.89 | form-M3 |
| 6 months | 3.34 | 99.92 | form-M3 |
| at 40 ± 2° C./75 ± 5% RH | | | |
| Initial | 3.59 | 99.92 | form-M3 |
| 1 months | 3.55 | 99.90 | form-M3 |
| 2 months | 3.33 | 99.90 | form-M3 |
| 3 months | 3.19 | 99.89 | form-M3 |
| 6 months | 3.00 | 99.91 | form-M3 |

It is believed that crystalline sofosbuvir form-M3 obtained by the processes disclosed herein may be a hydrate. It is further believed that the crystalline sofosbuvir form-M3 obtained by the processes disclosed herein may be a monohydrate.

In another aspect, the present invention provides a method for preparing amorphous sofosbuvir from the crystalline sofosbuvir form-M3 disclosed herein.

In one embodiment, amorphous sofosbuvir may be prepared by a process that includes the steps of:
a) dissolving crystalline sofosbuvir form-M3 in a solvent to form a solution; and
b) isolating amorphous sofosbuvir.

According to this embodiment, crystalline sofosbuvir form-M3 may be dissolved in a solvent to form a solution. In some embodiments, sofosbuvir may be dissolved in a solvent at an elevated temperature. For example, sofosbuvir may be dissolved in solvent at a temperature of about 20° C. to about 30° C.

Within the context of this embodiment, the solvent may be a water-miscible solvent such as methanol, ethanol, isopropyl alcohol, acetone, N,N-dimethylformamide, dimethylsulfoxide, or mixtures thereof. In particularly useful embodiments, the solvent is methanol.

Next, amorphous sofosbuvir may be isolated. This may be done by methods well-known to one of skill in the art. For example, isolation can be done using any techniques known in the art such as, for example, decantation, filtration (e.g., by gravity or suction), centrifugation, distillation, spray drying, agitated thin film drying (ATFD), or any combination thereof. In some embodiments, the solution is filtered and the filtrate is concentrated. In some particularly useful embodiments, concentration is performed under reduced pressure at about 45° C. to about 60° C. to obtain a solid and then stirred with n-heptane for about 2-3 hours.

Optionally, the solid may is washed and dried. In particular useful embodiments, the solid is isolated by filtration followed by washing with heptane and drying under vacuum.

Crystalline sofosbuvir form-M3 or amorphous sofosbuvir disclosed herein and prepared by the disclosed methods may be used to formulate an oral dosage form, such as a tablet or a capsule. When administered to patients, the sofosbuvir of the present invention may be useful treatment of individuals infected with hepatitis C. Sofosbuvir may be used singly or in combination with other anti-viral drugs, such as NS5A inhibitors. Particularly useful NS5A inhibitors include active ingredients such as ledipasvir, velpatasvir, and daclatasvir. In some embodiments, sofosbuvir may be combined with simeprevir to form a pharmaceutical dosage form.

The crystalline sofosbuvir form-M3 or amorphous sofosbuvir disclosed herein may be formulated into a tablet which may contain inactive ingredients such as colloidal silicon dioxide, polyvinylpyrrolidone (copovidone), croscarmellose sodium, lactose monohydrate, mannitol, magnesium stearate, and microcrystalline cellulose. The tablet may, in some embodiments, be coated with a film that includes additional excipients, artificial colors, and flavors. For example, a coating may contain polyethylene glycol, polyvinyl alcohol, talc, titanium dioxide, yellow iron oxide, red iron oxide, or mixtures thereof. One of skill in the art will be familiar with a variety of excipients and formulations that may be used to prepare desirable dosage forms with desired release characteristics and pharmacokinetic properties without undue experimentation.

Certain specific aspects and embodiments of the present application will be explained in greater detail with reference to the following examples, which are provided only for purposes of illustration and should not be construed as limiting the scope of the disclosure in any manner. Reasonable variations of the described procedures are intended to be within the scope of the present application. While particular aspects of the present application have been illustrated and described, it would be apparent to those skilled in the art that various other changes and modifications can be made without departing from the spirit and scope of the disclosure. It is therefore intended to encompass all such changes and modifications that are within the scope of this disclosure.

EXAMPLES

Example 1: Preparation of Crystalline Sofosbuvir Form-M3

Sofosbuvir (200 mg) was dissolved in N, N-dimethylformamide (0.4 mL) at 60-65° C. then cooled to 25-30° C. Water (1.4 mL) was added to this clear solution and the solvent was slowly evaporated off over several days. The solution was filtered to obtain a solid which was identified as crystalline sofosbuvir form-M3.

Example 2: Preparation of Crystalline Sofosbuvir Form-M3

Sofosbuvir was dissolved in 1,2-dimethoxyethane (16.2 mL) and water (10.8 mL). The solution was filtered through Hyflo and washed with mixture of 1,2-dimethoxyethane (1.8 mL) and water (1.2 mL). The obtained filtrate was added to another flask containing water (114 mL). The solution was seeded with crystalline sofosbuvir form-M3 (0.12 g) to precipitate a solid. After stirring at 20-25° C. for 16 hours, the solution was filtered, the obtained product was washed with water, then dried under reduced pressure to yield crystalline sofosbuvir form-M3 (3.0 g).

Example 3: Preparation of Crystalline Sofosbuvir Form-M3

Sofosbuvir crude (5 g) is dissolved in 1,2-dimethoxyethane (8.75 mL) and the solution is passed through Hyflo bed and washed with 1,2-dimethoxyethane (1.25 mL). The filtrate is added slowly to another flask having water (70 mL) and seeded with crystalline sofosbuvir form-M3 (0.1 g). The solution is stirred the contents for about 20 hours, filtered, washed with water, then dried at 40° C. to yield crystalline sofosbuvir form-M3.

Example 4: Preparation of Crystalline Sofosbuvir Form-M3

Sofosbuvir (10 g) and N,N-dimethylformamide (10 mL) were charged into round bottom flask at 25-30° C. The reaction mass was heated to 65° C. to get a clear solution which was then filtered to remove any undissolved particulate. The solution was then cooled to 25-30° C. Water (10 mL) was added to this clear solution, which was then seeded with crystalline sofosbuvir form-M3 (1% w/w) and stirred for 5-10 minutes. Water (60 mL) was added and the resulting reaction mixture was stirred at 25-30° C. for 3 hours. The solution was filtered to obtain a solid which was washed with water (20 mL) and dried at 30° C. under vacuum for 15 hours. The resulting product was identified as crystalline sofosbuvir form-M3.

Example 5: Preparation of Crystalline Sofosbuvir Form-M3

Sofosbuvir (10 g) and N,N-dimethylformamide (10 mL) were charged into round bottom flask at 25-30° C. The reaction mass was heated to 60° C. to get a clear solution which was filtered to remove undissolved particulate then cooled to 25-30° C. This solution was added to a mixture of water (70 mL) and crystalline sofosbuvir form-M3 seeds (1% w/w) at 25-30° C. and stirred at same temperature for 15 hours. The solution was filtered to obtain a solid which was washed with water (20 mL) and dried at 30° C. under vacuum for 2 hours. The resulting product was identified as crystalline sofosbuvir form-M3.

Example 6: Preparation of Crystalline Sofosbuvir Form-M3

Sofosbuvir (1 g) was dissolved in ethanol (2 mL) at 65° C.-70° C. and the solution was cooled to 25-30° C. Water (3 mL) was added to this clear solution, which was then seeded with crystalline sofosbuvir form-M3 (1% w/w). Water (7 mL) was then added and the solution was stirred for 15 hours. The solution was filtered to obtain a solid which was dried at 30° C. under vacuum for 2 hours. The resulting product was identified as crystalline sofosbuvir form-M3.

Example 7: Preparation of Crystalline Sofosbuvir Form-M3

Sofosbuvir (1 g) was dissolved in methanol (2 mL) at 65° C.-70° C. and the solution was cooled to 25-30° C. Water (3 mL) was added to this clear solution which was then seeded with crystalline sofosbuvir form-M3 (1% w/w). Water (7 mL) was then added and the solution was stirred for 15 hours. The solution was filtered to obtain a solid which was then dried at 30° C. under vacuum for 2 hours. The resulting product was identified as crystalline sofosbuvir form-M3.

Example 8: Preparation of Crystalline Sofosbuvir Form-M3

Sofosbuvir (1 g) was dissolved in isopropyl alcohol (2 mL) at 65° C.-70° C. and the solution was cooled to 25-30° C. Water (3 mL) was added to this clear solution which was then seeded with crystalline sofosbuvir form-M3 (1% w/w) before adding more water (7 mL) and stirring for 15 hours. The solution was filtered to obtain a solid which was then dried at 30° C. under vacuum for 2 hours. The resulting product was identified as crystalline sofosbuvir form-M3.

Example 9: Preparation of Crystalline Sofosbuvir Form-M3

Sofosbuvir (1 g) was dissolved in acetone (2 mL) at 65° C.-70° C. and the solution was cooled to 25-30° C. Water (3 mL) was added to this clear solution which was then seeded with crystalline sofosbuvir form-M3 (1% w/w). Water (7 mL) was added and the solution was stirred for 15 hours. The solution was filtered to obtain a solid which was then dried at 30° C. under vacuum for 2 hours. The resulting product was identified as crystalline sofosbuvir form-M3.

Example 10: Preparation of Crystalline Sofosbuvir Form-M3

Sofosbuvir (1 g) was dissolved in dimethyl sulfoxide (1 mL) at 65° C.-70° C. and the solution was cooled to 25-30° C. Water (2 mL) was added to the solution which was then seeded with crystalline sofosbuvir form-M3 (1% w/w). Water (8 mL) was added and the solution was stirred for 15 hours. The solution was filtered and the obtained solid was dried at 30° C. under vacuum for 2 hours. The resulting product was identified as crystalline sofosbuvir form-M3.

Example 11: Preparation of Amorphous Sofosbuvir

Crystalline sofosbuvir form-M3 (3 g) was dissolved in methanol (24 mL). The solution was filtered and the obtained filtrate was concentrated under reduced pressure at ~50° C. to get a frothing solid, which was stirred with n-heptane (21 mL) for 2 hours. The solution was filtered and the obtained product was washed with n-heptane, then dried under reduced pressure to yield amorphous sofosbuvir (2.8 g).

We claim:

1. A crystalline sofosbuvir form-M3, characterized by a PXRD pattern having peaks at 2θ angle positions of 7.61, 16.92, and 20.47±0.2°.
2. The crystalline sofosbuvir form-M3 of claim 1, wherein the PXRD pattern has additional peaks at 2θ angle positions of 14.19, 17.98, 19.58, and 23.27±0.2°.
3. A crystalline sofosbuvir form-M3, characterized by a PXRD pattern as shown in FIG. 1.
4. A pharmaceutical dosage form comprising the crystalline sofosbuvir form-M3 according to claim 3.
5. The dosage form of claim 4 further comprising a pharmaceutically acceptable excipient.
6. The crystalline sofosbuvir form-M3 according to claim 1, further characterized by a DSC thermogram having a peak at about 72.88° C. to 75.51° C.
7. A pharmaceutical dosage form comprising the crystalline sofosbuvir form-M3 according to claim 1.
8. The dosage form of claim 7 further comprising a pharmaceutically acceptable excipient.
9. A process for the preparation of crystalline sofosbuvir form-M3, the process comprising:
   a. dissolving sofosbuvir in a solvent to form a solution, wherein said solvent comprises a water-miscible solvent;
   b. adding an anti-solvent to the solution; and
   c. isolating crystalline sofosbuvir form-M3.
10. The process according to claim 9, wherein the crystalline sofosbuvir form-M3 is characterized by a PXRD pattern having peaks at 2θ angle positions of 7.61, 16.92, and 20.47±0.2°.
11. The process according to claim 9, wherein the solvent further comprises water.
12. The process according to claim 9, wherein the water-miscible solvent is selected from the group consisting of methanol, ethanol, isopropanol, 1-butanol, isobutanol, 1-pentanol, acetone, acetonitrile, N,N-dimethylformamide, dimethylsulfoxide, 1,2-dimethoxyethane, and mixtures thereof.
13. The process according to claim 9, wherein the anti-solvent is water.
14. The process according to claim 9, further comprising the step of stirring after adding anti-solvent and before the isolating step.
15. The process according to claim 9, wherein the solution is seeded with crystalline sofosbuvir form-M3 after adding an anti-solvent and before the isolating step.
16. The process according to claim 15, wherein the solvent is selected from the group consisting of methanol, ethanol, isopropanol, 1-butanol, isobutanol, 1-pentanol, N,N-dimethylformamide, dimethyl sulfoxide, 1,2-dimethoxyethane, acetone, and mixtures thereof.
17. The process according to claim 15, wherein the anti-solvent is water.
18. The process according to claim 11, wherein the water-miscible solvent is selected from the group consisting of methanol, ethanol, isopropanol, 1-butanol, isobutanol, 1-pentanol, acetone, acetonitrile, N,N-dimethylformamide, dimethylsulfoxide, 1,2-dimethoxyethane, and mixtures thereof.
19. A process according to claim 15, wherein additional anti-solvent is added to the solution after the solution is seeded with crystalline sofosbuvir form-M3 and before the isolating step.
20. The process according to claim 9, wherein seeds of sofosbuvir form-M3 are suspended in the anti-solvent prior to adding to the solution.

* * * * *